(12) United States Patent
Adachi

(10) Patent No.: US 11,432,704 B2
(45) Date of Patent: Sep. 6, 2022

(54) IMAGE PICKUP APPARATUS AND ENDOSCOPE

(71) Applicant: OLYMPUS CORPORATION, Tokyo (JP)

(72) Inventor: Fumiyuki Adachi, Koganei (JP)

(73) Assignee: OLYMPUS CORPORATION, Tokyo (JP)

( * ) Notice: Subject to any disclaimer, the term of this patent is extended or adjusted under 35 U.S.C. 154(b) by 399 days.

(21) Appl. No.: 16/576,910

(22) Filed: Sep. 20, 2019

(65) Prior Publication Data

US 2020/0015667 A1 Jan. 16, 2020

Related U.S. Application Data

(63) Continuation of application No. PCT/JP2018/004636, filed on Feb. 9, 2018.

(30) Foreign Application Priority Data

May 19, 2017 (JP) .............................. JP2017-099553

(51) Int. Cl.
*A61B 1/00* (2006.01)
*A61B 1/05* (2006.01)
*G06T 1/00* (2006.01)

(52) U.S. Cl.
CPC ........ *A61B 1/00009* (2013.01); *A61B 1/0005* (2013.01); *A61B 1/00006* (2013.01);
(Continued)

(58) Field of Classification Search
CPC ... A61B 1/05; A61B 1/00006; A61B 1/00009; A61B 1/00018; A61B 1/0005;
(Continued)

(56) References Cited

U.S. PATENT DOCUMENTS 4,873,572 A 10/1989 Miyazaki et al.
8,194,121 B2 6/2012 Blumzvig et al.
(Continued)

FOREIGN PATENT DOCUMENTS

JP S63-210813 A 9/1988
JP H08-294062 A 11/1996
(Continued)

OTHER PUBLICATIONS

International Search Report dated Mar. 13, 2018 issued in PCT/JP2018/004636.

*Primary Examiner* — Ryan N Henderson
(74) *Attorney, Agent, or Firm* — Scully, Scott, Murphy & Presser, P.C.

(57) ABSTRACT

An image pickup apparatus includes: a plurality of image pickup devices configured to pick up images of a same object and sequentially read the images for each line; an objective optical system configured to form the images at different image-forming positions on the image pickup devices; a memory configured to record predetermined time differences for reading the leading positions of the effective pixels of the images at the same timing; and an I2C control circuit configured to control the image reading timing of the image pickup devices by generating a plurality of synchronizing signals based on a master synchronizing signal and supplying the synchronizing signals to the image pickup devices after shifting the synchronizing signals by the respective predetermined time differences.

7 Claims, 10 Drawing Sheets

(52) U.S. Cl.
CPC ...... *A61B 1/00018* (2013.01); *A61B 1/00096* (2013.01); *A61B 1/05* (2013.01); *G06T 1/0085* (2013.01); *G06T 2207/10021* (2013.01); *G06T 2207/30004* (2013.01)

(58) Field of Classification Search
CPC . A61B 1/00096; A61B 1/00193; A61B 1/045; A61B 1/00004; A61B 1/000094; A61B 1/000095; A61B 1/000096; A61B 1/00011; A61B 1/00013; A61B 1/00016; A61B 1/00045; A61B 1/041; A61B 1/04; G06T 1/0085; G06T 2207/10021; G06T 2207/30004; G02B 23/2423; G02B 23/2415; H04N 2005/2255; H04N 5/2258
See application file for complete search history.

(56) References Cited

U.S. PATENT DOCUMENTS

| | | | |
|---|---|---|---|
| 11,257,590 B2 * | 2/2022 | Granneman | A61B 1/045 |
| 2005/0267328 A1 | 12/2005 | Blumzvig et al. | |
| 2014/0160259 A1 * | 6/2014 | Blanquart | H04N 5/374 |
| | | | 348/65 |
| 2014/0340496 A1 * | 11/2014 | Okawa | A61B 1/00057 |
| | | | 600/103 |
| 2016/0262596 A1 | 9/2016 | Ogihara et al. | |
| 2018/0253532 A1 * | 9/2018 | Granneman | G16H 40/63 |

FOREIGN PATENT DOCUMENTS

| | | | | |
|---|---|---|---|---|
| JP | H11-56757 A | 3/1999 | | |
| JP | 2002-306406 A | 10/2002 | | |
| JP | 2005-525896 A | 9/2005 | | |
| JP | 2012-050602 A | 3/2012 | | |
| JP | 2014-140594 A | 8/2014 | | |
| JP | 2014140594 A * | 8/2014 | ........... | H04N 13/239 |
| WO | WO 03/098913 A2 | 11/2003 | | |
| WO | WO 2016/035401 A1 | 3/2016 | | |

* cited by examiner

IMAGE PICKUP APPARATUS AND ENDOSCOPE

CROSS REFERENCE TO RELATED APPLICATION

This application is a continuation application of PCT/JP2018/004636 filed on Feb. 9, 2018 and claims benefit of Japanese Application No. 2017-099553 filed in Japan on May 19, 2017, the entire contents of which are incorporated herein by this reference.

BACKGROUND OF THE INVENTION

1. Field of the Invention

The present invention relates to an image pickup apparatus including a plurality of image pickup devices configured to sequentially read images for each line, and an endoscope.

2. Description of the Related Art

Conventionally, endoscopes are configured to pick up images of an object in a subject and endoscope systems include image processors configured to generate object observation images picked up by endoscopes. Such endoscopes and such endoscope systems have been widely used in a medical field and an industrial field.

For an endoscope of such an endoscope system, an image pickup device (e.g., a CMOS image sensor) driven by a predetermined clock signal is conventionally used. Moreover, an endoscope including a cable disposed to transmit an image pickup signal outputted from an image pickup device is known.

Furthermore, recently used 3D endoscopes are configured to pick up images of an object from different points of view by using two left and right image pickup optical systems and image pickup devices. For a 3D endoscope including such left and right image pickup devices, a configuration where the image pickup devices are transversely mounted to reduce a diameter of an insertion portion is used. Namely, the image pickup devices are horizontally placed with respect to an insertion axis of the insertion portion (for example, see the specification of U.S. Pat. No. 8,194,121).

For example, if two substrates having the respective left and right image pickup devices are disposed in the insertion portion, the two substrates are disposed, for example, perpendicularly to the insertion portion. This configuration is used to reduce the diameter of the insertion portion. If the substrates having the image pickup devices are disposed perpendicularly to the insertion portion, object images picked up by the left and right image pickup devices are inverted.

A CMOS image sensor has an inverse reading function of inverting reading in a vertical direction. Thus, if the image pickup devices are CMOS image sensors, vertical reading of one of the image pickup devices is inverted, so that even inverted object images can be read in the same direction.

SUMMARY OF THE INVENTION

An image pickup apparatus according to an aspect of the present invention includes: a plurality of image pickup devices configured to pick up images of a same object and sequentially read the images for each line; an optical system configured to form the images at different image-forming positions on the plurality of image pickup devices; a memory configured to record information on predetermined time differences in consideration of a difference in number of leading lines among a plurality of effective pixels in order to change image reading timing for reading the plurality of effective pixels at the same timing from leading positions of the plurality of effective pixels picked up at different image-forming positions by the plurality of image pickup devices; and a timing control circuit configured to control the image reading timing of the plurality of image pickup devices by generating a plurality of synchronizing signals based on a master synchronizing signal from a processor so as to independently control the image reading timing of the plurality of image pickup devices, and supplying the plurality of synchronizing signals to the plurality of image pickup devices after shifting the plurality of synchronizing signals from the master synchronizing signal by the respective predetermined time differences from the memory in order to align the leading positions of the effective pixels picked up at the different image-forming positions by the plurality of image pickup devices and read the leading positions of the effective pixels at the same timing.

An endoscope according to an aspect of the present invention includes: the image pickup apparatus; and an insertion portion insertable into a subject, wherein the plurality of image pickup devices and the optical system are disposed in a distal end portion of the insertion portion.

DETAILED DESCRIPTION OF THE PREFERRED EMBODIMENT(S)

Preferred embodiments of the present invention will be specifically described below with reference to the accompanying drawings.

Embodiment 1

Figure 1:
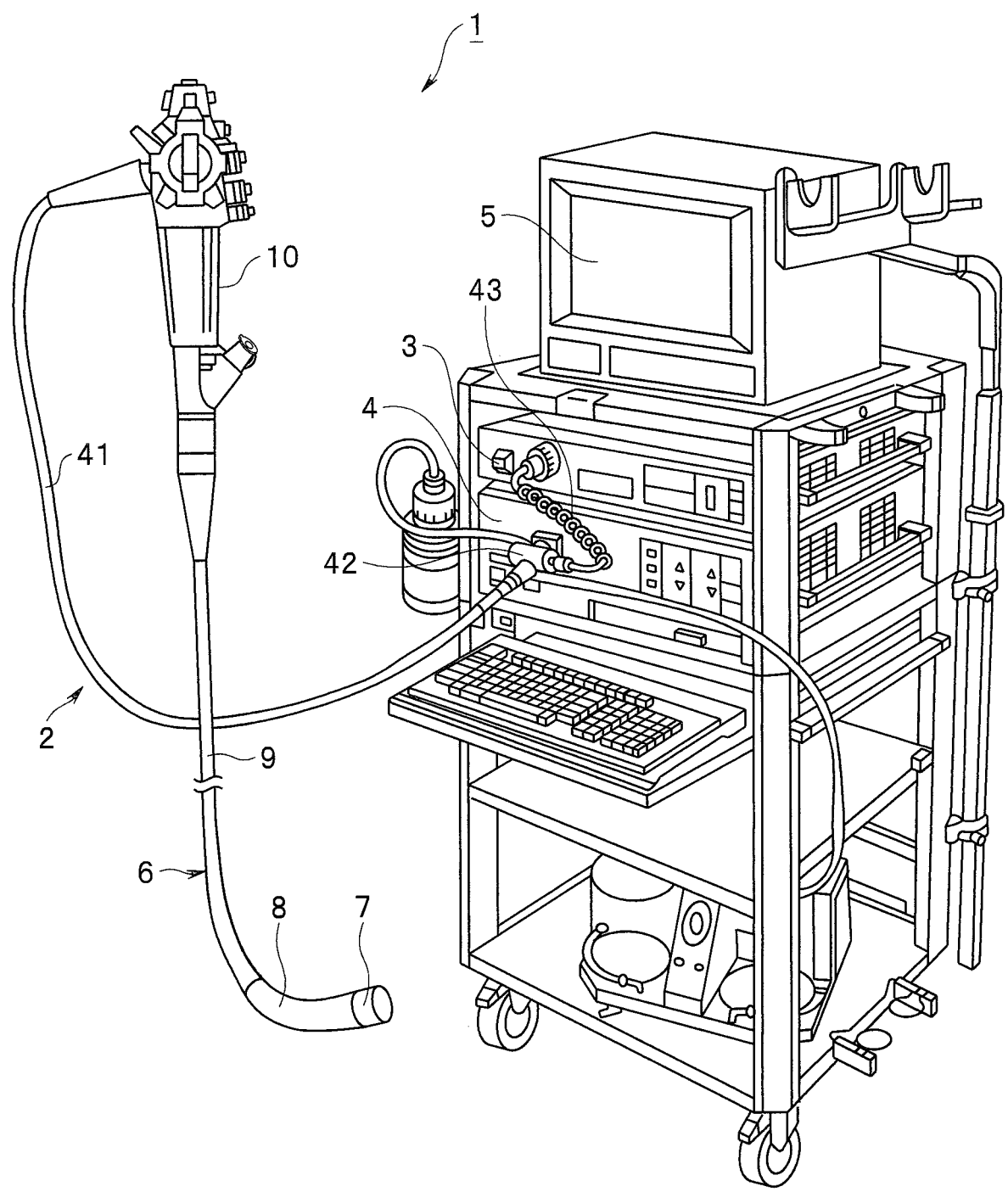
FIG. 1 illustrates a configuration of an endoscope system including an image pickup apparatus (endoscope) according to Embodiment 1 of the present invention.

FIG. 1 illustrates a configuration of an endoscope system including an image pickup apparatus (endoscope) according to Embodiment 1 of the present invention. In the present embodiment, an endoscope that has a solid-state image pickup device and picks up an image of an object in a subject will be described as an image pickup apparatus.

As illustrated in FIG. 1, an endoscope system 1 having the image pickup apparatus (endoscope) of Embodiment 1 includes an endoscope 2 configured to observe a subject and output an image pickup signal, a video processor 3 that is connected to the endoscope 2 and performs predetermined image processing on the image pickup signal from the endoscope 2, a light source apparatus 4 configured to supply light for illuminating the subject, and a monitor apparatus 5 configured to display an observation image corresponding to the image pickup signal.

The endoscope 2 includes elongated insertion portion 6 inserted into, for example, a body cavity of the subject, an endoscope operation portion 10 that is disposed on a proximal end side of the insertion portion 6 and is operated by an operator who grasps the endoscope operation portion 10, and a universal cord 41 having one end extending from a side of the endoscope operation portion 10.

The insertion portion 6 has a rigid distal end portion 7 provided on a distal end of the insertion portion 6, a bending portion 8 provided to bend on a rear end of the distal end portion 7, and a long and flexible tube portion 9 provided on a rear end of the bending portion 8.

A connector 42 is provided on a proximal end of the universal cord 41. The connector 42 is connected to the light source apparatus 4. In other words, a pipe sleeve (not illustrated) serving as a connecting end portion of a fluid pipe projecting from a distal end of the connector 42 and a lightguide pipe sleeve (not illustrated) serving as a supply end portion of illumination light are detachably connected to the light source apparatus 4.

Moreover, one end of a connecting cable 43 is connected to an electric contact portion provided on a side surface of the connector 42. The connecting cable 43 contains, for example, a signal line configured to transmit the image pickup signal from the endoscope 2. A connector portion on the other end of the connecting cable 43 is connected to the video processor 3.

In the connector 42, a connector circuit 51 (see FIG. 3) is disposed, which will be described later. A configuration of the connector circuit 51 will be discussed later.

Figure 2A:
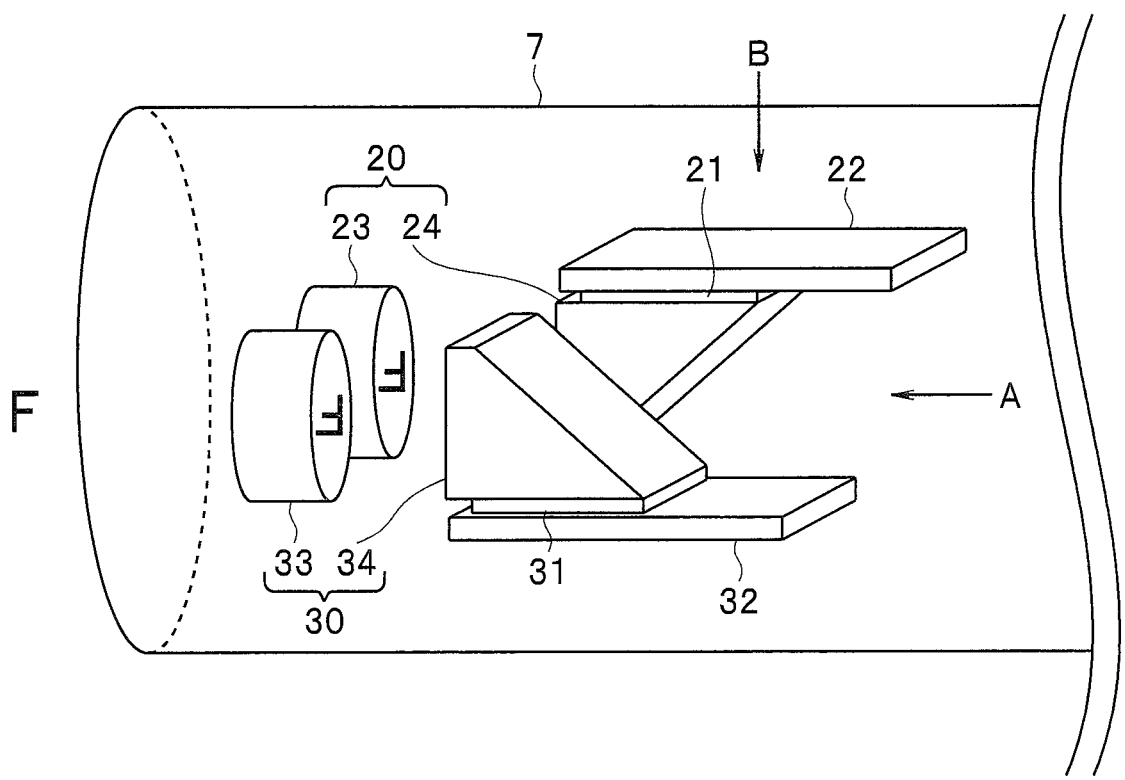
FIG. 2A is a perspective view illustrating a configuration of a distal end portion of an insertion portion according to Embodiment 1.
Figure 2B:
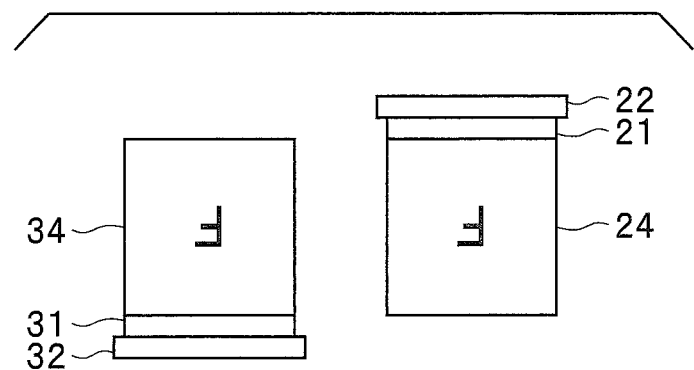
FIG. 2B is a view of FIG. 2A taken in a direction of an arrow A (rear direction)
Figure 2C:
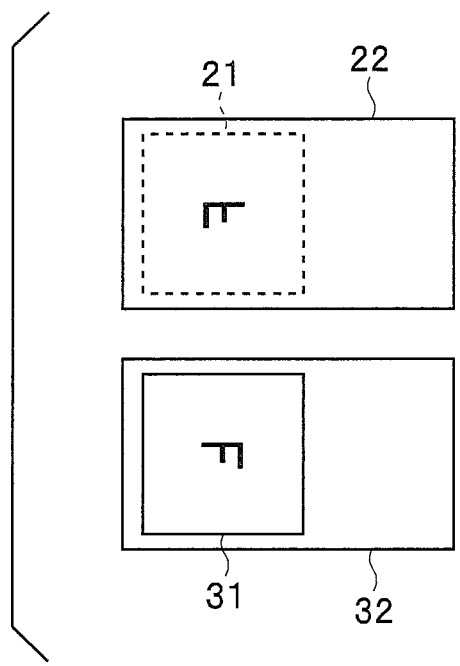
FIG. 2C is a view of FIG. 2A taken in a direction of an arrow B (top direction)

A configuration of the distal end portion 7 of the insertion portion 6 will be described below. FIG. 2A is a perspective view illustrating a configuration of the distal end portion of the insertion portion according to Embodiment 1. FIG. 2B is a view of FIG. 2A taken in a direction of an arrow A (rear direction). FIG. 2C is a view of FIG. 2A taken in a direction of an arrow B (top direction).

As illustrated in FIGS. 2A to 2C, a right-eye objective optical system 20, an image pickup device 21 placed on an image-forming plane of the objective optical system 20, and a substrate 22 where the image pickup device 21 is placed are disposed in the distal end portion 7 of the insertion portion 6. Furthermore, a left-eye objective optical system 30, an image pickup device 31 placed on an image-forming plane of the objective optical system 30, and a substrate 32 where the image pickup device 31 is placed are disposed in the distal end portion 7 of the insertion portion 6.

The objective optical system 20 includes an objective lens 23 and a prism 24. The objective optical system 30 includes an objective lens 33 and a prism 34. The objective optical system 20 is not limited to a configuration including the objective lens 23 and the prism 24. For example, the objective optical system 20 may include a plurality of objective lenses and a prism. The objective optical system 30 is not limited to a configuration including the objective lens 33 and the prism 34. For example, the objective optical system 30 may include a plurality of objective lenses and a prism.

The prism 24 is a right-angle prism disposed behind the objective lens 23. The prism 24 totally reflects light that is reflected from an object and passes through the objective lens 23, and then the prism 24 directs the light to the image pickup device 21. Likewise, the prism 34 is a right-angle prism disposed behind the objective lens 33. The prism 34 totally reflects light that is reflected from an object and passes through the objective lens 33, and then the prism 34 directs the light to the image pickup device 31.

In the present embodiment, in order to reduce the diameter of the insertion portion 6, the substrate 22 is disposed in an upper side of the distal end portion 7 and the substrate 32 is disposed in a lower side of the distal end portion 7. The configuration vertically inverts an object image picked up by the image pickup device 21 through the right-eye objective optical system 20 and an object image picked up by the image pickup device 31 through the left-eye objective optical system 30. In other words, the objective optical systems 20 and 30 form images vertically inverted on the image pickup devices 21 and 31. In this way, the objective optical systems 20 and 30 constitute an optical system configured to form images at different image-forming positions on the image pickup devices 21 and 31.

Figure 3:
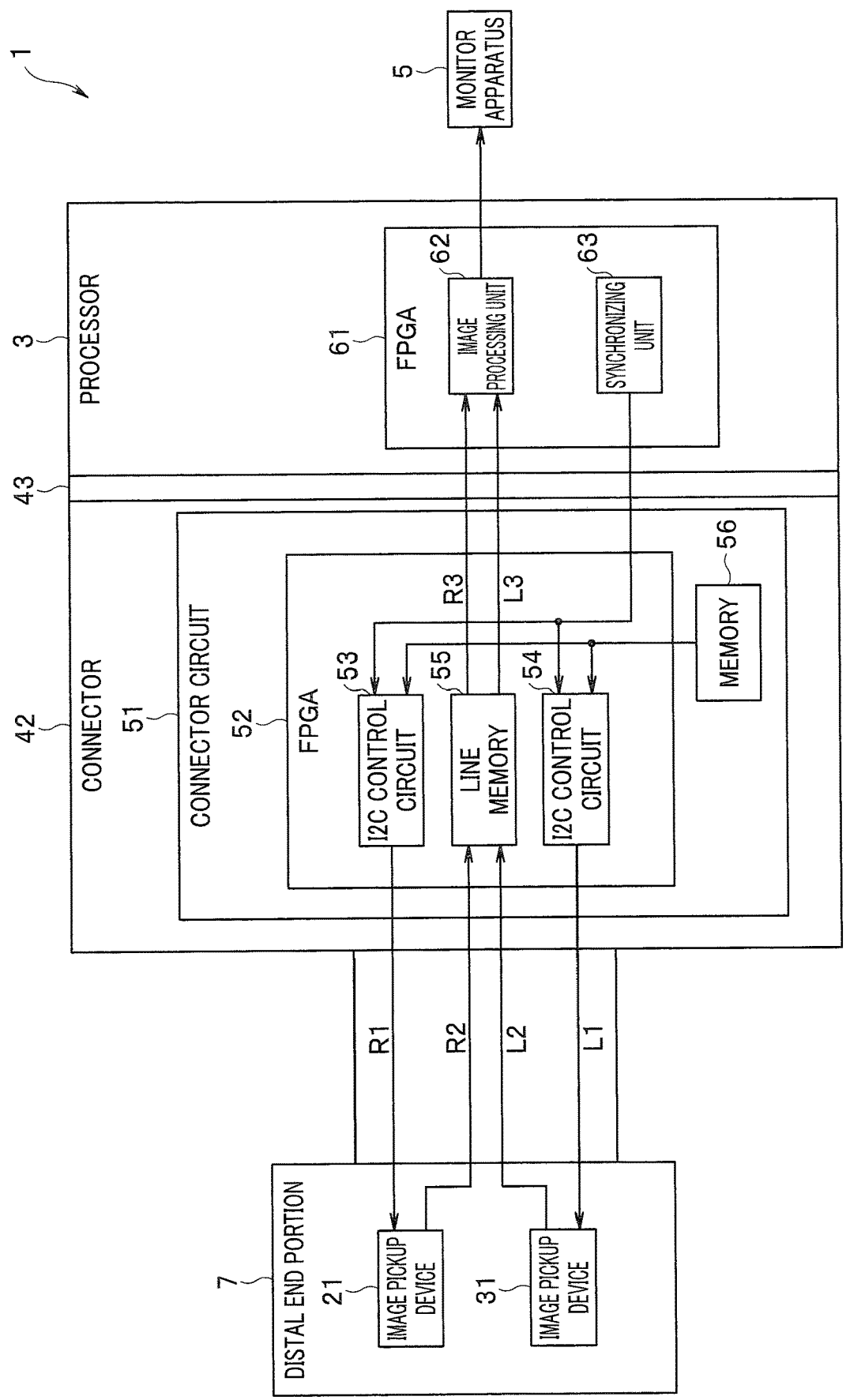
FIG. 3 is a block diagram illustrating an electrical configuration of the endoscope system according to Embodiment 1.

Referring to FIG. 3, an electrical configuration of the endoscope system 1 according to Embodiment 1 will be described below. FIG. 3 is a block diagram illustrating the electrical configuration of the endoscope system according to Embodiment 1.

As described above, the image pickup devices 21 and 31 are disposed in the distal end portion 7. The image pickup devices 21 and 31 in the present embodiment are solid-state image pickup devices of a rolling shutter technique, that is, image pickup devices each of which include a CMOS image sensor configured to sequentially read images for each line.

As illustrated in FIG. 3, the connector circuit 51 is disposed in the connector 42. The connector circuit 51 includes an FPGA 52 and a memory 56. The FPGA 52 includes a so-called FPGA (field programmable gate array). The FPGA 52 has a function of controlling circuits in the endoscope 2 in response to operation control from the video processor 3 in addition to functions of driving the image pickup devices 21 and 31 and processing the image pickup signals from the image pickup devices 21 and 31. The FPGA 52 includes an I2C control circuit 53, an I2C control circuit 54, and a line memory 55.

The video processor 3 includes an FPGA 61. The FPGA 61 includes an image processing unit 62 and a synchronizing unit 63.

The synchronizing unit 63 outputs a master synchronizing signal for controlling the driving of the image pickup devices 21 and 31, to the I2C control circuits 53 and 54. The memory 56 stores information for changing timing of reading (information on predetermined time differences) between the image pickup devices 21 and 31. The information on the predetermined time differences is inputted to the I2C control circuits 53 and 54.

The I2C control circuit 53 generates a synchronizing signal R1 according to the master synchronizing signal from the synchronizing unit 63 and the information on the predetermined time differences from the memory 56 and outputs the signal to the image pickup device 21. The I2C control circuit 54 generates a synchronizing signal L1 according to the master synchronizing signal from the synchronizing unit 63 and the information on the predetermined time differences from the memory 56 and outputs the signal to the image pickup device 31.

For one frame, a relationship of $\Delta t = R \times \Delta L/L$ is established where $\Delta t$ is the predetermined time difference, $\Delta L$ is a difference in the number of lines regarding leading lines among effective pixels, L is a total number of lines in one frame, and R is a frame rate.

The synchronizing signal R1 and the synchronizing signal L1 are synchronizing signals read at a timing changed according to the information on the predetermined time differences from the memory 56. Thus, in the present embodiment, the regions of the effective pixels of the image pickup device 21 and the image pickup device 31 are controlled to be read at the same timing. The synchronizing signals R1 and L1 in the present embodiment are transmitted by a so-called I2C (Inter-Integrated Circuit).

In this way, the I2C control circuits 53 and 54 constitute a timing control circuit configured to control timing of reading images of the image pickup devices 21 and 31 in order to align leading positions of effective pixels at the same position of an object picked up by the image pickup devices 21 and 31 and read the leading positions of the effective pixels.

Video data R2 picked up by the image pickup device 21 and video data L2 picked up by the image pickup device 31 are inputted to the line memory 55. The line memory 55 performs processing for matching of video formats of the video data R2 and the video data L2 and outputs video data R3 and video data L3 in matching video formats to the image processing unit 62 of the video processor 3. The line memory 55 outputs the video data R3 and the video data L3 after performing processing for changing the position of optical black (OB) or replacing the optical black, which will be discussed in detail later.

The image processing unit 62 merges the video data R3 for a right eye and the video data L3 for a left eye and outputs the merged video data to the monitor apparatus 5. Thus, stereoscopic video is displayed with a parallax on the monitor apparatus 5.

Figure 4:
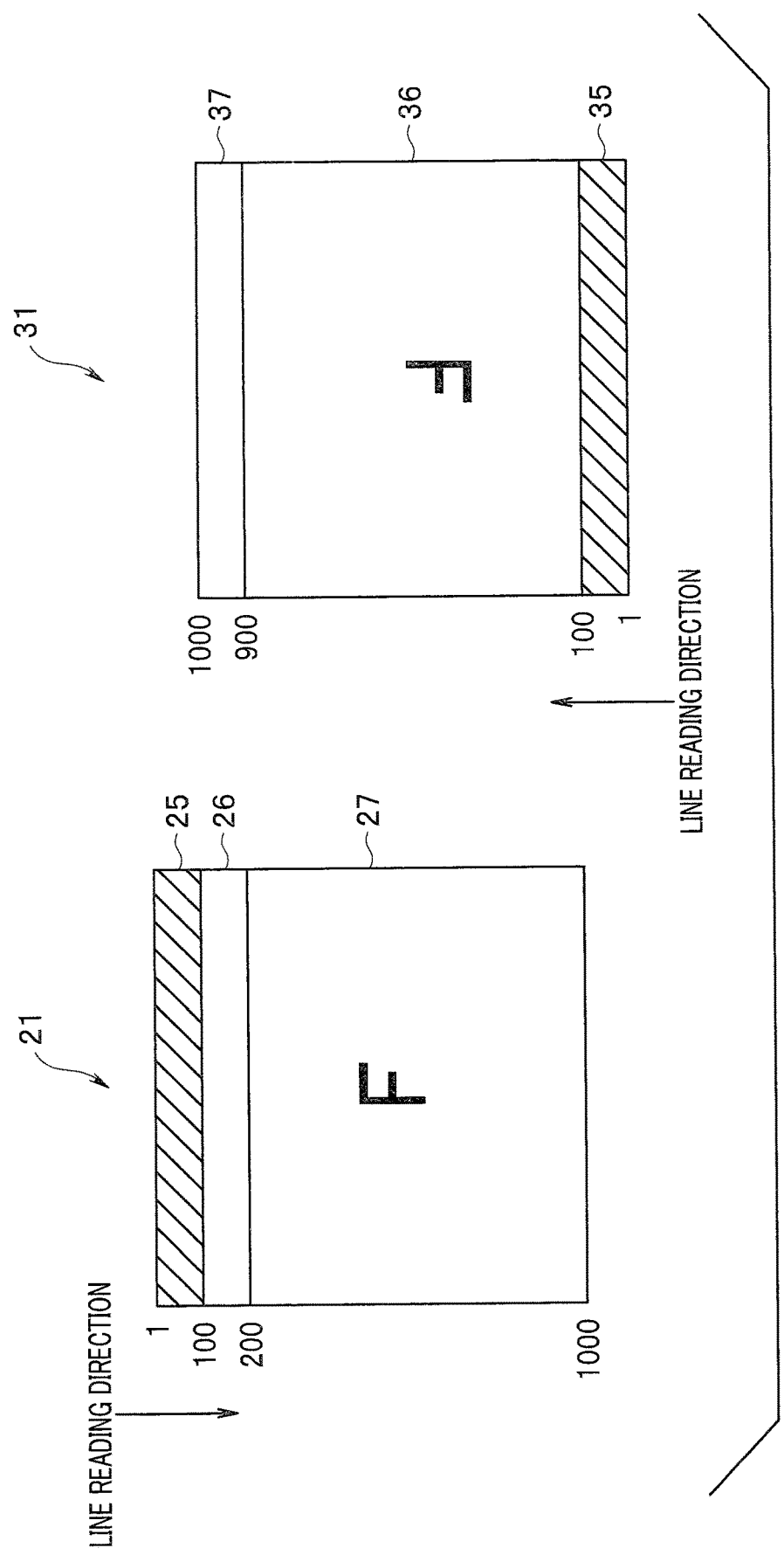
FIG. 4 is an explanatory drawing of an example of image pickup regions of image pickup devices 21 and 31.
Figure 5:
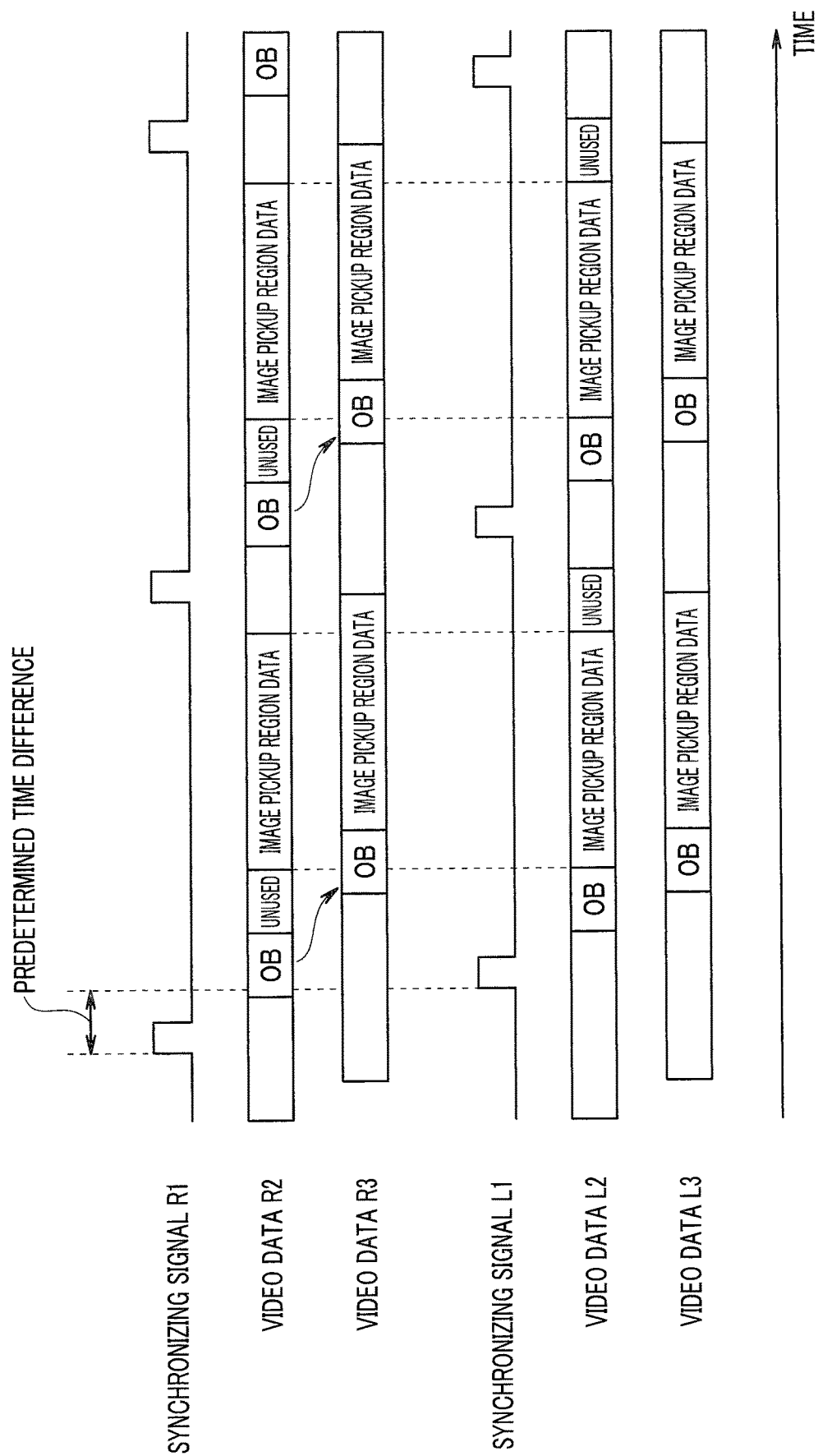
FIG. 5 is a timing chart for explaining an example of timing of reading data by the image pickup devices 21 and 31.

Referring to FIGS. 4 to 5, the operations of the endoscope system 1 configured thus will be described below. FIG. 4 is an explanatory drawing of an example of image pickup regions of the image pickup devices 21 and 31. FIG. 5 is a timing chart for explaining an example of the timing of reading data by the image pickup devices 21 and 31.

As illustrated in FIG. 4, in the image pickup device 21, 1 to 100 lines constitute an optical black region 25, 101 to 200 lines constitute an unused data region 26, and 201 to 1000 lines constitute an effective pixel region 27.

In the image pickup device 31, 1 to 100 lines constitute an optical black region 35, 101 to 900 lines constitute an effective pixel region 36, and 901 to 1000 lines constitute an unused data region 37.

In this way, the image pickup device 21 and the image pickup device 31 have effective pixels in different lines. Thus, when the image pickup device 21 and the image pickup device 31 start reading at the same timing, pixels at the same position in the image pickup device 21 and the image pickup device 31 cannot be read at the same timing. In other words, the effective pixel region 27 of the image pickup device 21 starts from the 201st line, whereas the effective pixel region 36 of the image pickup device 31 starts from the 101st line, so that reading of the effective pixel region 36 by the image pickup device 31 is advanced by 100 lines from reading by the image pickup device 21. Put another way, the image pickup device 31 starts reading after a delay of 100 lines from the image pickup device 21, so that the reading of the effective pixel region 36 can be started at the same timing as the effective pixel region 27 of the image pickup device 21.

As described above, the information on the predetermined time differences for starting reading by the image pickup device 31 after a delay of 100 lines from the image pickup device 21 (that is, information for controlling the timing of reading) is stored in the memory 56 and the information is inputted to the I2C control circuits 53 and 54. Thus, according to the information for controlling the timing of reading from the memory 56, the I2C control circuits 53 and 54 generate the synchronizing signals R1 and L1 so as to read the effective pixel region 27 of the image pickup device 21 and the effective pixel region 36 of the image pickup device 31 at the same timing.

Consequently, as shown in FIG. 5, the synchronizing signal L1 outputted from the I2C control circuit 54 is generated after a delay of the predetermined time difference from the synchronizing signal R1 outputted from the I2C control circuit 53.

In response to the synchronizing signal R1, the image pickup device 21 outputs the video data R2 to the line memory 55. In the video data R2, OB data (OB pixels) of the optical black region 25, unused data (unused pixels) of the unused data region 26, and image pickup region data (effective pixels) of the effective pixel region 27 are sequentially read. In response to the synchronizing signal L1, the image pickup device 31 outputs the video data L2 to the line memory. In the video data L2, OB data (OB pixels) of the optical black region 35, image pickup region data (effective pixels) of the effective pixel region 36, and unused data (unused pixels) of the unused data region 37 are sequentially read.

The synchronizing signal L1 is shifted from the synchronizing signal R1 by the predetermined time difference, so that the image pickup region data of the image pickup device 21 and the image pickup region data of the image pickup device 31 are read at the same timing.

The line memory 55 temporarily stores the video data R2 outputted from the image pickup device 21 and outputs the video data R3, in which OB data is attached immediately before the image pickup region data, to the image processing unit 62 of the video processor 3. Moreover, the line memory 55 temporarily stores the video data outputted from the image pickup device 31 and outputs the video data L3 to the image processing unit 62 of the video processor 3. Thus, the video data R3 and L3 in matching video formats are inputted to the image processing unit 62. Therefore, the image processing unit 62 of the video processor 3 can generate stereoscopic video with a parallax only by merging the video data R3 and the video data L3.

As described above, the endoscope 2 of the present embodiment generates the synchronizing signals R1 and L1 for independently controlling the image pickup devices 21 and 31 according to the information on the predetermined time difference in the memory 56, and reads the effective pixel region 27 of the image pickup device 21 and the effective pixel region 36 of the image pickup device 31 at the same timing. Therefore, according to the endoscope (image pickup apparatus) of the present embodiment, pixel information at the same position of the image pickup devices configured for sequential reading can be read at the same timing.

Embodiment 2

Embodiment 2 will be described below.

Figure 6:
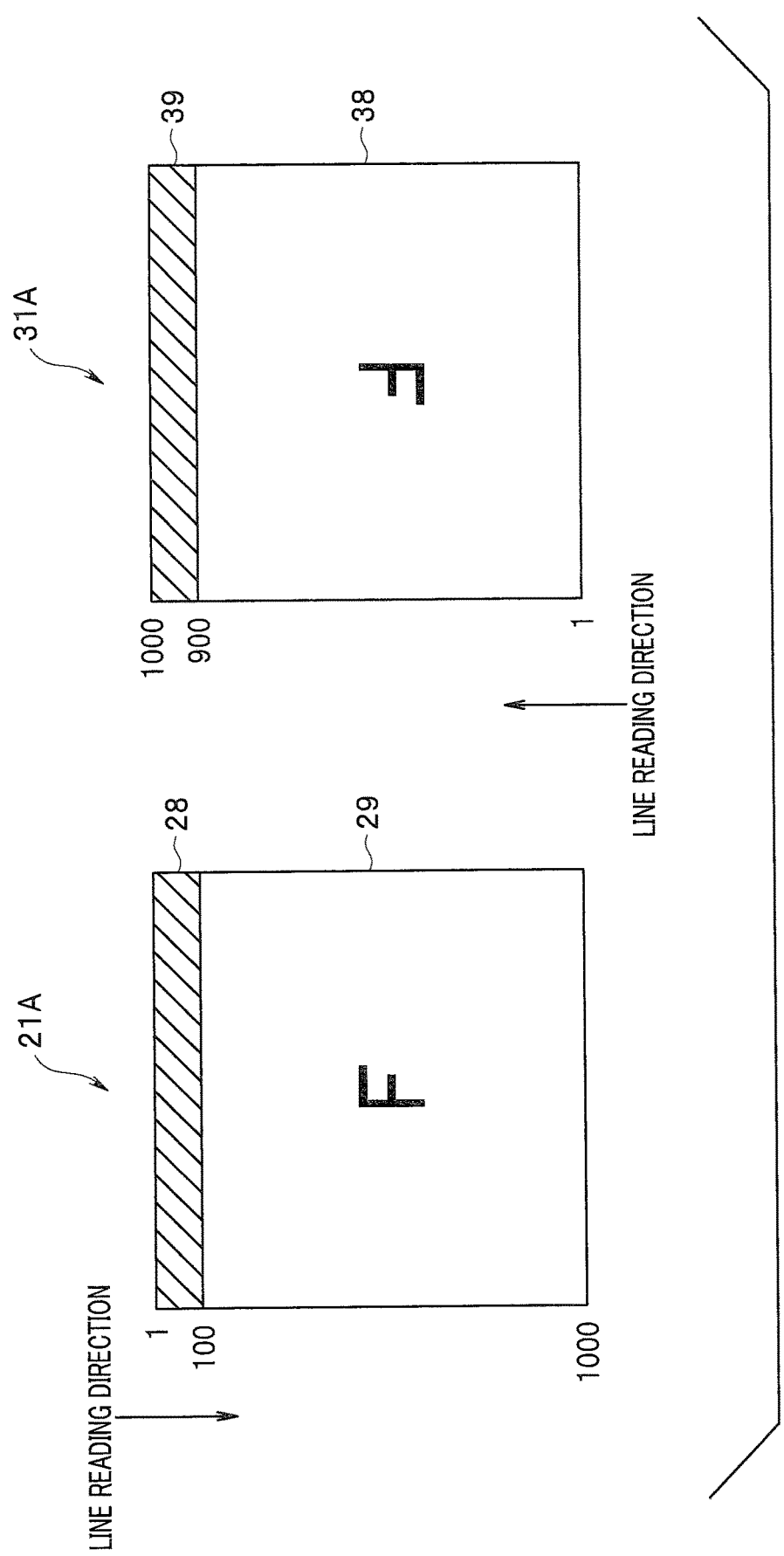
FIG. 6 is an explanatory drawing of an example of image pickup regions of image pickup devices according to Embodiment 2.

An overall configuration of an endoscope system 1 according to Embodiment 2 is identical to the configuration of Embodiment 1. Embodiment 2 is different from Embodiment 1 in a configuration of an image pickup device. FIG. 6 is an explanatory drawing of an example of image pickup regions of the image pickup devices according to Embodiment 2.

As illustrated in FIG. 6, an endoscope system 1 of Embodiment 2 includes image pickup devices 21A and 31A instead of the image pickup devices 21 and 31 of Embodiment 1. The image pickup devices 21A and 31A have optical black regions disposed in the same direction.

In the image pickup device 21A, 1 to 100 lines constitute an optical black region 28 and 101 to 1000 lines constitute an effective pixel region 29. In the image pickup device 31A, 1 to 900 lines constitute an effective pixel region 38 and 901 to 1000 lines constitute an optical black region 39.

Figure 7:
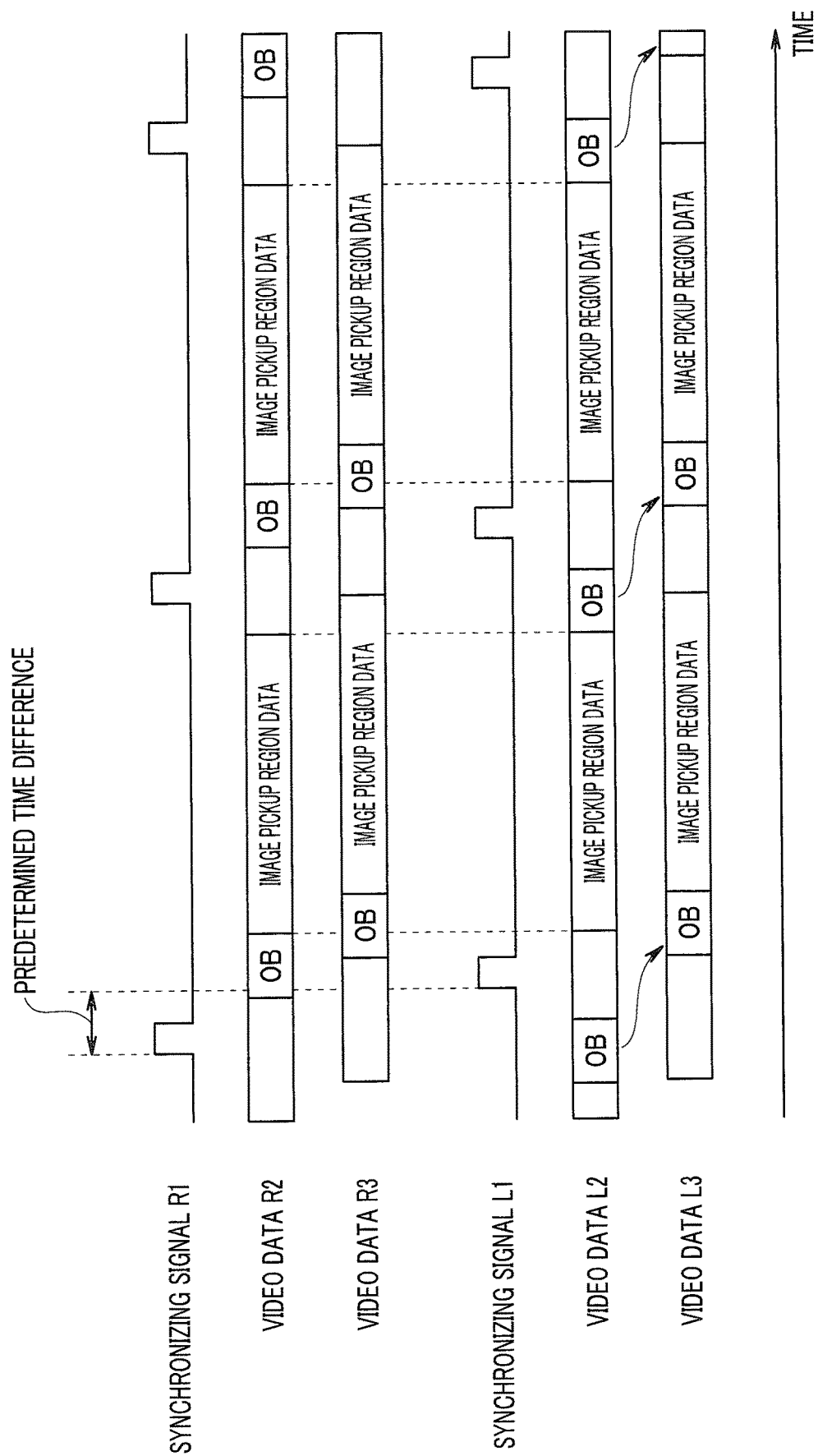
FIG. 7 is a timing chart for explaining an example of timing of reading data by image pickup devices 21A and 31A.

FIG. 7 is a timing chart for explaining an example of timing of reading data by the image pickup devices 21A and 31A.

A process of generating synchronizing signals R1 and L1 by I2C control circuits 53 and 54 is similar to the process of Embodiment 1. The synchronizing signals R1 and L1 are generated so as to read image pickup region data of the image pickup devices 21A and 31A at the same timing. In other words, the synchronizing signal L1 outputted from the I2C control circuit 54 is generated after a delay of a predetermined time difference from the synchronizing signal R1 outputted from the I2C control circuit 53.

In response to the synchronizing signal R1, the image pickup device 21A outputs video data R2 to a line memory 55. In the video data R2, OB data of the optical black region 28 and image pickup region data of the effective pixel region 29 are sequentially read. In response to the synchronizing signal L1, the image pickup device 31A outputs video data L2 to the line memory 55. In the video data L2, image pickup region data of the effective pixel region 38 and OB data of the optical black region 39 are sequentially read.

The line memory 55 generates the video data R3 and L3 in matching video formats. Specifically, the line memory 55 controls the video data L2 such that OB data of video data in a previous frame is attached to a beginning of image pickup region data in a current frame. Thus, video data R3 and L3 in matching video formats are outputted from the line memory 55 and are inputted to an image processing unit 62 of a video processor 3. Other components and operations are similar to the components and operations of Embodiment 1.

Therefore, according to the endoscope (image pickup apparatus) of the present embodiment, pixel information at the same position of the image pickup devices configured for sequential reading can be read at the same timing as in Embodiment 1.

Embodiment 3

Embodiment 3 will be described below.

In Embodiment 1, the two substrates 22 and 32 are disposed in the distal end portion 7, whereas in Embodiment 3, a single substrate is disposed in a distal end portion 7. In other words, in Embodiment 3, the substrate where two image pickup devices are disposed serves as a common substrate.

Figure 8A:
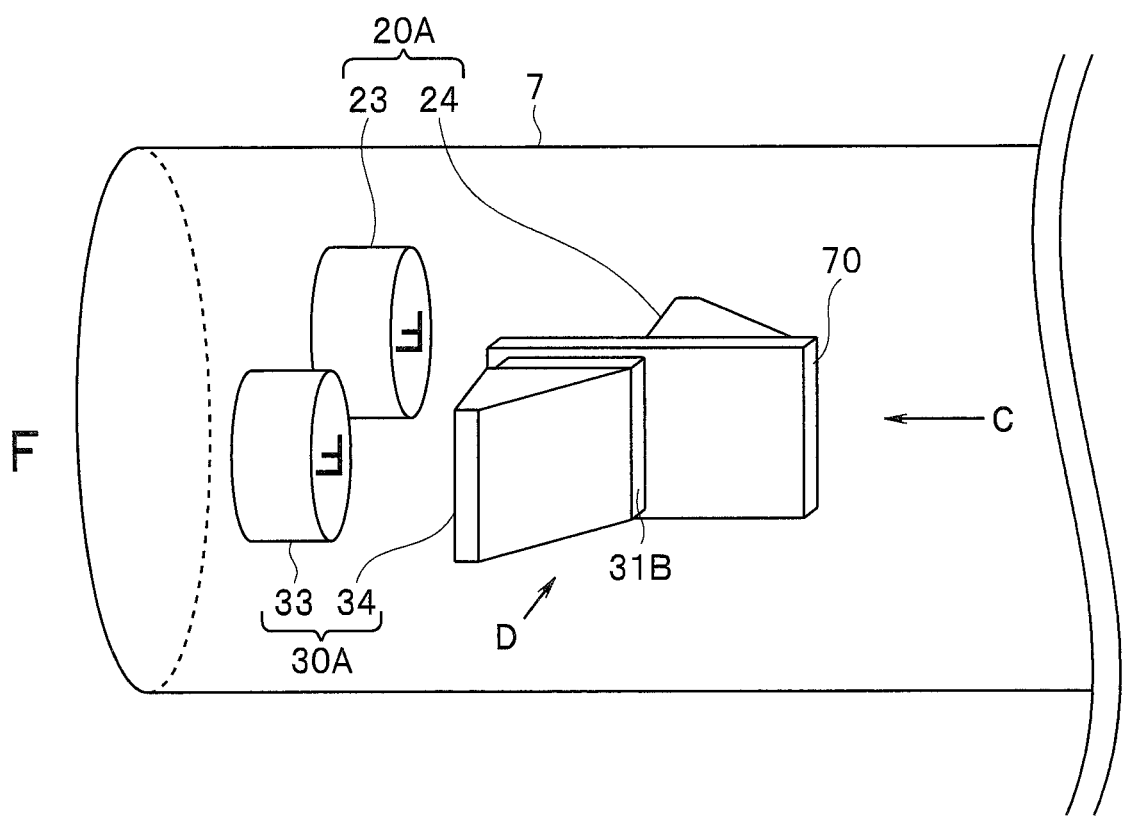
FIG. 8A is a perspective view illustrating a configuration of a distal end portion of an insertion portion according to Embodiment 3.
Figure 8B:
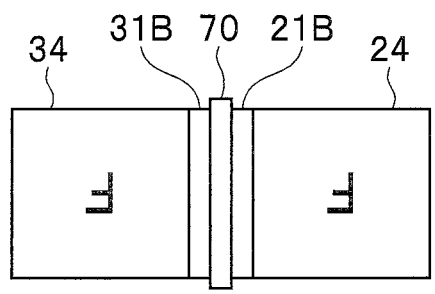
FIG. 8B is a view of FIG. 8A taken in a direction of an arrow C (rear direction)
Figure 8C:
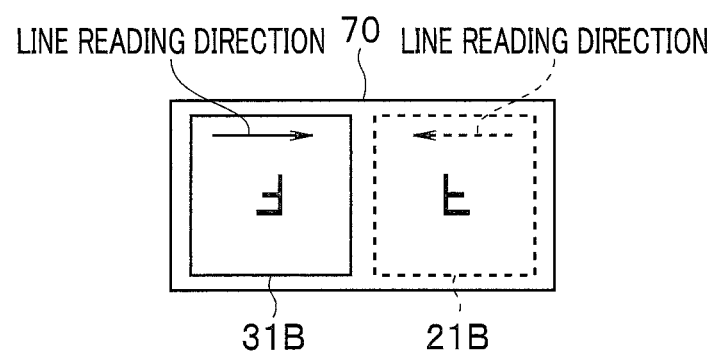
FIG. 8C is a view of FIG. 8A taken in a direction of an arrow D (width direction).

FIG. 8A is a perspective view illustrating a configuration of the distal end portion of an insertion portion according to Embodiment 3. FIG. 8B is a view of FIG. 8A taken in a direction of an arrow C (rear direction). FIG. 8C is a view of FIG. 8A taken in a direction of an arrow D (width direction).

As illustrated in FIGS. 8A to 8C, a right-eye objective optical system 20A and an image pickup device 21B placed on an image-forming plane of the objective optical system 20A are disposed in the distal end portion 7 of an insertion portion 6. Moreover, a left-eye objective optical system 30A and an image pickup device 31B placed on an image-forming plane of the objective optical system 30A are disposed in the distal end portion 7. Furthermore, in the distal end portion 7, a substrate 70 is disposed, the image pickup device 21B is disposed on one surface of the substrate 70, and the image pickup device 31B is disposed on the other surface of the substrate 70.

The objective optical system 20A includes an objective lens 23 and a prism 24 as in FIG. 2A. The objective optical system 30A includes an objective lens 33 and a prism 34 as in FIG. 2A. However, a layout of the prisms 24 and 34 is different from a layout of FIGS. 2A to 2C. In the present embodiment, the prisms 24 and 34 are disposed to totally reflect light in a direction of a central axis of the insertion portion 6, the light being reflected from an object.

The configuration horizontally inverts an object image picked up by the image pickup device 21B through the right-eye objective optical system 20A and an object image picked up by the image pickup device 31B through the left-eye objective optical system 30A. In other words, the objective optical systems 20A and 30A form images horizontally inverted on the image pickup devices 21B and 31B.

Other components and control of timing of reading image data are similar to the components and the control of timing of reading in Embodiment 1. The endoscope of the present embodiment obtains the same effect as in Embodiment 1 and includes the single substrate 70 provided in the distal end portion, so that the insertion portion 6 can be smaller in diameter than in Embodiment 1.

The present invention is not limited to the embodiments described above and can be changed or modified in various ways within the scope of the present invention.

What is claimed is:

1. An image pickup apparatus comprising:
    a plurality of image pickup devices configured to sequentially read image data for each line;
    an optical system configured to form a plurality of images related to a same object on the plurality of image pickup devices, the plurality of formed images being at different image-forming positions;
    a memory configured to record information on predetermined time differences, the predetermined time differences being differences of timings at which leading positions of effective pixels are read respectively in a plurality of image data, when the plurality of image data are read at the same time, the plurality of image data being acquired by the plurality of image pickup devices picking up respective images of the plurality of formed images; and
    a timing control circuit configured to generate a plurality of synchronizing signals shifted respectively by the predetermined time differences based on a master synchronizing signal from a processor, wherein in the plurality of image pickup devices, reading timings of the image data are independently controlled based on the plurality of synchronizing signals.

2. The image pickup apparatus according to claim 1, wherein a relationship of $\Delta t = R \times \Delta L/L$ is established, where $\Delta t$ is each of the predetermined time differences, $\Delta L$ is a difference in the number of lines regarding leading lines between the effective pixels in the plurality of image data, L is a total number of lines in one frame, and R is a frame rate.

3. The image pickup apparatus according to claim 1, wherein the plurality of image pickup devices comprises a first image pickup device and a second image pickup device, the first image pickup device outputs a first video data in which an optical black pixel, an unused pixel, and each of the effective pixels are sequentially read, and the second image pickup device outputs a second video data in which an optical black pixel, each of the effective pixels, and an unused pixel are sequentially read.

4. The image pickup apparatus according to claim 3, further comprising a line memory configured to perform processing for matching video formats of the first video data and the second video data, wherein the line memory attaches the optical black pixel of the first video data immediately before each of the effective pixels of the first video data.

5. The image pickup apparatus according to claim 1, wherein the plurality of image pickup devices comprises a first image pickup device and a second image pickup device, the first image pickup device outputs a first video data in which an optical black pixel and each of the effective pixels are sequentially read, and the second image pickup device outputs a second video data in which each of the effective pixels and an optical black pixel are sequentially read.

6. The image pickup apparatus according to claim 5, further comprising a line memory configured to perform processing for matching video formats of the first video data and the second video data, wherein the line memory attaches the optical black pixel of the second video data in a previous frame immediately before each of the effective pixels of the second video data in a current frame.

7. An endoscope comprising:

the image pickup apparatus according to claim 1; and an insertion portion insertable into a subject, wherein the plurality of image pickup devices and the optical system are disposed in a distal end portion of the insertion portion.

* * * * *